US012708279B2

(12) United States Patent
Kremeier

(10) Patent No.: US 12,708,279 B2
(45) Date of Patent: Aug. 18, 2026

(54) METHOD AND SYSTEM FOR FILLING AN ESOPHAGUS BALLOON

(71) Applicant: Loewenstein Medical Technology S.A., Luxembourg (LU)

(72) Inventor: Peter Kremeier, Karlsruhe (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 952 days.

(21) Appl. No.: 17/932,376

(22) Filed: Sep. 15, 2022

(65) Prior Publication Data

US 2023/0081811 A1 Mar. 16, 2023

(30) Foreign Application Priority Data

Sep. 16, 2021 (DE) ........................ 102021004686.2

(51) Int. Cl.
*A61B 5/03* (2006.01)
*A61B 5/00* (2006.01)
(Continued)

(52) U.S. Cl.
CPC ............ *A61B 5/037* (2013.01); *A61B 5/0803* (2013.01); *A61B 5/6853* (2013.01);
(Continued)

(58) Field of Classification Search
CPC ..... A61B 5/037; A61B 5/0803; A61B 5/6853; A61B 2505/03; A61B 2560/0276;
(Continued)

(56) References Cited

U.S. PATENT DOCUMENTS 5,697,375 A * 12/1997 Hickey ................ A61B 5/0215 600/528
5,862,802 A * 1/1999 Bird .................... A61M 16/021 128/204.21

(Continued)

FOREIGN PATENT DOCUMENTS

WO WO-9300037 A1 * 1/1993 ............. A61B 5/037
WO WO-2005077268 A1 * 8/2005 .......... A61M 16/026
WO WO-2018217516 A1 * 11/2018 .......... A61B 5/6876

OTHER PUBLICATIONS

Francesco Mojoli et al, “In vivo calibration of esophageal pressure in the mechanically ventilated patient makes measurements reliable”, Critical Care, (Apr. 11, 2016), vol. 20, No. 1, doi: 10.1186/s13054-016-1278-5.

(Continued)

*Primary Examiner* — Wesley G Harris
(74) *Attorney, Agent, or Firm* — Abel Schillinger, LLP

(57) ABSTRACT

Method for ascertaining and setting a filling volume of a balloon of a catheter, which is placed in the esophagus of a living being, wherein the balloon is filled and/or emptied using a fluid. According to the invention, the balloon is filled and/or emptied step-by-step using at least two volume steps, a pressure difference between a pressure at the end of an expiration (Pmin) and a pressure at the end of an inspiration (Pmax) is determined for at least two volume steps, a relative pressure difference between Pmin and Pmax is determined, a border range is defined on the basis of the relative pressure difference, and an optimum filling volume is ascertained in consideration of the border range.

19 Claims, 4 Drawing Sheets

(51) Int. Cl.
*A61B 5/08* (2006.01)
*A61J 15/00* (2006.01)

(52) U.S. Cl.
CPC ....... *A61J 15/0088* (2015.05); *A61B 2505/03* (2013.01); *A61B 2560/0276* (2013.01); *A61B 2562/0247* (2013.01); *A61J 2200/76* (2013.01)

(58) Field of Classification Search
CPC .......... A61B 2562/0247; A61J 15/0088; A61J 2200/76; A61M 2016/0027; A61M 16/024; A61M 2210/105; A61M 2205/3344; A61M 16/0003; A61M 2205/3334
See application file for complete search history.

(56) References Cited

U.S. PATENT DOCUMENTS

2009/0088735 A1 4/2009 Abboud et al.
2009/0120439 A1* 5/2009 Goebel ............... A61M 16/202 128/204.21
2010/0043795 A1* 2/2010 Ujhazy ............. A61M 16/0057 128/204.23
2015/0038958 A1 2/2015 Jackson et al.
2017/0231572 A1* 8/2017 Lowery ................ A61B 5/4839 600/301
2018/0221608 A1* 8/2018 Schwaibold ........ A61M 16/024
2020/0260985 A1* 8/2020 Kremeier ............... A61B 5/053
2021/0016035 A1* 1/2021 Euliano, II ........... A61B 5/7282

OTHER PUBLICATIONS

Yan-Lin Yang et al, “Optimal esophageal balloon volume for accurate estimation of pleural pressure at end- expiration and end-inspiration: an in vitro bench experiment”, Intensive Care Medicine Experimental, Biomed Central Ltd, London, UK, (Aug. 2, 2017), vol. 5, No. 1, doi: 10.1186/S40635-017-0148-Z, pp. 1-12.
Hotz Justin C et al., “Measurements Obtained From Esophageal Balloon Catheters Are Affected by the Esophageal Balloon Filling Volume in Children With ARDS”, Respiratory Care, US, (Oct. 31, 2017), vol. 63, No. 2, doi:10.4187/respcare.05685, ISSN 0020-1324, pp. 177-186.
Chiumello et al., Am J Respir Crit Care Med, vol. 178, pp. 346-355.

* cited by examiner

METHOD AND SYSTEM FOR FILLING AN ESOPHAGUS BALLOON

CROSS-REFERENCE TO RELATED APPLICATIONS

The present application claims priority under 35 U.S.C. § 119 of German Patent Application Nos. 102021004686.2, filed Sep. 16, 2021, the entire disclosure of which is expressly incorporated by reference herein.

BACKGROUND OF THE INVENTION

1. Field of the Invention

The invention relates to a method and system for filling an esophagus balloon.

2. Discussion of Background Information

When critically ill patients have to be ventilated over a longer period of time, a lung-protective ventilation strategy is required. The goal of a lung-protective ventilation strategy is to keep the effects of the mechanical pressure and volume stress of the lung under ventilation as minor as possible. The adaptation of the ventilation to the individual regional lung function and to the ventilation need of the patient has to be regularly evaluated, since a "lung-protective" ventilation significantly improves the survival rate of patients having acute respiratory distress syndrome (ARDS).

It is considered certain that the respiration-synchronous collapse and reopening of lung areas ("atelectasis trauma") in ARDS patients is one of the main factors for respiration-associated lung damage and represents an independent risk factor for higher mortality. An optimally set PEEP is a basic condition for lung-protective ventilation to minimize respiratory-cyclic opening and collapse ("alveolar cycling"). At excessively low PEEP values, lung compartments are damaged by atelectasis trauma, at excessively high PEEP and uniform "driving pressure" they are damaged due to over-expansion (volume trauma) of predominantly ventral lung areas.

For the extent of the mechanical stress load on the alveoli and thus for the ventilation-associated lung damage, the inspiratory plateau pressure set on the respirator (ventilation pressure at the end of the inspiration) is not decisive, but rather the transpulmonary pressure (TPP), defined as the difference of ventilation pressure and pleural pressure.

The bedside measurement of the esophageal pressure (Peso) was in the past reserved for scientific questions. In the meantime, modern intensive respirators and novel balloon catheters permit this measuring method to be carried out in a minimally invasive manner and in this way to supply valuable items of information about the present ventilation status. The changes of the esophageal pressure during a breathing cycle reflect the changes of the pleural pressure here.

Chiumello et al. (Am J Respir Crit Care Med 178; 346-355, 2008), the entire disclosure of which is incorporated by reference herein, were able to show that due to the high variability of the ratio of lung elastance to thorax wall elastance, an inspiratory plateau pressure set on the respirator resulted in very different values for the transpulmonary pressure gradient. In patients having elevated pleural pressure, for example, as a result of an elevated intraabdominal pressure, the same inspiratory pressure can be accompanied by less ventilation-associated lung damage than in patients having low pleural pressure. If the transpulmonary pressure becomes negative, the formation of atelectasis occurs. A decisive aspect of the effect of PEEP is maintaining a positive end-expiratory transpulmonary pressure.

Under machine ventilation, the inspiratory plateau pressure (Pplat) or the end-expiratory pressure (PEEP) are used as surrogate parameters for the calculation of the inspiratory or expiratory alveolar pressure, and the esophageal pressure (Peso) is used for the pleural pressure.

The esophageal pressure is measured via a commercially available, nasally introduced balloon catheter, which also functions as a feeding tube. The pressure probe is connected to the pressure transducer of the respirator. The balloon filling has particular significance for ensuring a valid measurement setup and thus a reliable esophageal pressure measurement. If the balloon is overfilled or underfilled, incorrectly esophageal measured values and thus also invalid transpulmonary pressures are indicated.

The correct filling volume of the esophagus balloon is as decisive as the correct location of the balloon. Since the measured esophageal pressure values are directly dependent thereon, they have to be produced individually by patient. The standard filling indicated by several authors is probably not correct and results in incorrect measured values.

It has been shown that the standard volume is not ideal for each patient and the optimum volume can change depending on individual patient parameters, location of the patient, and the like. The filling volume is ideally to be selected such that the perfusion of the inner wall of the esophagus is not impaired and nonetheless reliable measurement results are obtained.

The bedside filling is complex and time-intensive and requires outstanding practical experience of the medical personnel. There is therefore a demand for a method for ascertaining and maintaining an optimum filling volume of esophagus balloons.

SUMMARY OF THE INVENTION

The invention provides a method for ascertaining and setting a filling volume of a balloon of a catheter, which is placed in the esophagus of a living being, wherein the balloon is filled and/or emptied using a fluid. According to the invention, the method comprises the following method steps:

- step-by-step filling and/or emptying of the balloon using at least two volume steps
- determining a pressure difference between a pressure at the end of an expiration Pmin and a pressure at the end of an inspiration Pmax for at least two volume steps
- determining a relative pressure difference between Pmin and Pmax
- defining a border range on the basis of the relative pressure difference
- ascertaining an optimum filling volume in consideration of the border range.

In some embodiments, the method is characterized in that the balloon is filled and/or emptied via at least one pressure source, wherein the pressure source provides fluid in the form of a gas and fills and/or empties the balloon using gas.

In some embodiments, the method is characterized in that the balloon is filled and/or emptied via at least one pressure source, wherein the pressure source provides fluid in the form of a gas, preferably in the form of air, and fills and/or empties the balloon using air.

In some embodiments, the method is characterized in that the balloon is filled using a standard volume and is subsequently completely emptied again. In some embodiments, the method is characterized in that the balloon is initially filled using a standard volume and is subsequently completely emptied again. In some embodiments, the method is characterized in that the balloon pressure is ascertained when the balloon has initially been filled using a standard volume.

In some embodiments, the method is characterized in that the balloon is filled step-by-step with gas after the emptying using at least two volume steps.

In some embodiments, the method is characterized in that the balloon is filled step-by-step with gas until the balloon is slightly overinflated.

In some embodiments, the method is characterized in that the balloon is filled step-by-step with gas until the balloon has a balloon pressure of approximately 10 to approximately 40 mbar, preferably of approximately 20 to approximately 40 mbar, particularly preferably of approximately 30 mbar.

In some embodiments, the method is characterized in that the balloon is emptied step-by-step with at least two volume steps.

In some embodiments, the method is characterized in that the balloon is emptied step-by-step until the balloon preferably no longer contains gas. In some embodiments, the method is characterized in that the balloon is emptied step-by-step until the balloon no longer contains air.

In some embodiments, the method is characterized in that the balloon is filled and/or emptied depending on the volume step with approximately 0.1 mL to approximately 2 mL gas, preferably with approximately 0.2 mL to approximately 0.8 mL, particularly preferably with approximately 0.5 mL.

In some embodiments, the method is characterized in that after at least one volume step, in each case at least one breath is waited out before the balloon is filled and/or emptied with a further volume step.

In some embodiments, the method is characterized in that after each volume step, in each case 1 to approximately 10 breaths are waited out, preferably approximately 2 to approximately 5 breaths, particularly preferably 3 breaths.

In some embodiments, the method is characterized in that the balloon pressure is ascertained continuously and/or at specific points in time.

In some embodiments, the method is characterized in that the balloon pressure is ascertained at the end of the expiration Pmin and/or at the end of the inspiration Pmax of each breath of each volume step.

In some embodiments, the method is characterized in that the ascertained balloon pressures Pmin for each volume step are averaged and the ascertained balloon pressures Pmax for each volume step are averaged.

In some embodiments, the method is characterized in that the pressure difference between the pressure at the end of the expiration Pmin and the pressure at the end of the inspiration Pmax is ascertained for at least one, preferably for all volume steps.

In some embodiments, the method is characterized in that the relative pressure difference from one volume step to a next volume step is ascertained as a percentage value or index value.

In some embodiments, the method is characterized in that the pressures of Pmin and Pmax within the border range run nearly constant and in parallel to one another.

In some embodiments, the method is characterized in that the border range is a percentage value or index value, wherein the border range is less than 100%, preferably less than approximately 50%, particularly preferably less than approximately 25%.

In some embodiments, the method is characterized in that the border range is in a range from 0 to approximately 10% inclusive.

In some embodiments, the method is characterized in that a minimum filling volume and/or a maximum filling volume is ascertained.

In some embodiments, the method is characterized in that the minimum filling volume and/or the maximum filling volume is ascertained on the basis of the border range.

In some embodiments, the method is characterized in that the filling volume, at which the relative pressure difference is within the border range for the first time, is defined as the minimum filling volume.

In some embodiments, the method is characterized in that the filling volume, at which the relative pressure difference is within the border range for the last time, is defined as the maximum filling volume.

In some embodiments, the method is characterized in that the optimum filling volume is defined in a range between the minimum filling volume and the maximum filling volume.

In some embodiments, the method is characterized in that the optimum filling volume is more than approximately 10% above the minimum filling volume and less than approximately 80% below the maximum filling volume.

In some embodiments, the method is characterized in that the optimum filling volume is more than approximately 20% above the minimum filling volume and less than approximately 50% below the maximum filling volume.

In some embodiments, the method is characterized in that the optimum filling volume is approximately 30% above the minimum filling volume and approximately 70% below the maximum filling volume.

In some embodiments, the method is characterized in that the balloon is filled using the optimum filling volume, wherein the optimum filling volume ensures a reliable, valid, reproducible pressure transfer from the lung to the balloon.

In some embodiments, the method is characterized in that an esophageal compliance is ascertained on the basis of the balloon pressure at the end of the expiration at the minimum filling volume and on the basis of the balloon pressure at the end of the expiration at the maximum filling volume.

In some embodiments, the method is characterized in that a corrected optimum filling volume is ascertained with incorporation of the ascertained esophageal compliance and the optimum filling volume.

In some embodiments, the method is characterized in that the optimum filling volume and/or the corrected optimum filling volume is set and maintained.

In some embodiments, the method is characterized in that the balloon pressure and/or the filling volume is monitored to detect a leak.

In some embodiments, the method is characterized in that a leak compensation is carried out if a leak is detected.

In a further aspect, the invention provides a system for ascertaining and setting a filling volume of a balloon of a catheter which is placed in the esophagus of a living being. The system comprises the catheter, at least one pressure source having a control unit, at least one line via which the catheter and the pressure source are pneumatically connected to one another, and at least one sensor. According to the invention, the system is configured and designed to execute the method according to the invention.

In some embodiments, the system is characterized in that the pressure source is a ventilator and/or an anesthesia machine.

BRIEF DESCRIPTION OF THE DRAWINGS

Exemplary embodiments of the system 100 according to the invention and of the method according to the invention are shown in the drawings. In the drawings:

FIG. 2 shows an esophageal catheter, wherein FIG. 2A shows a schematic side view of the catheter and FIG. 2B shows a cross section according to line S-S through a section of a hose of the catheter.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
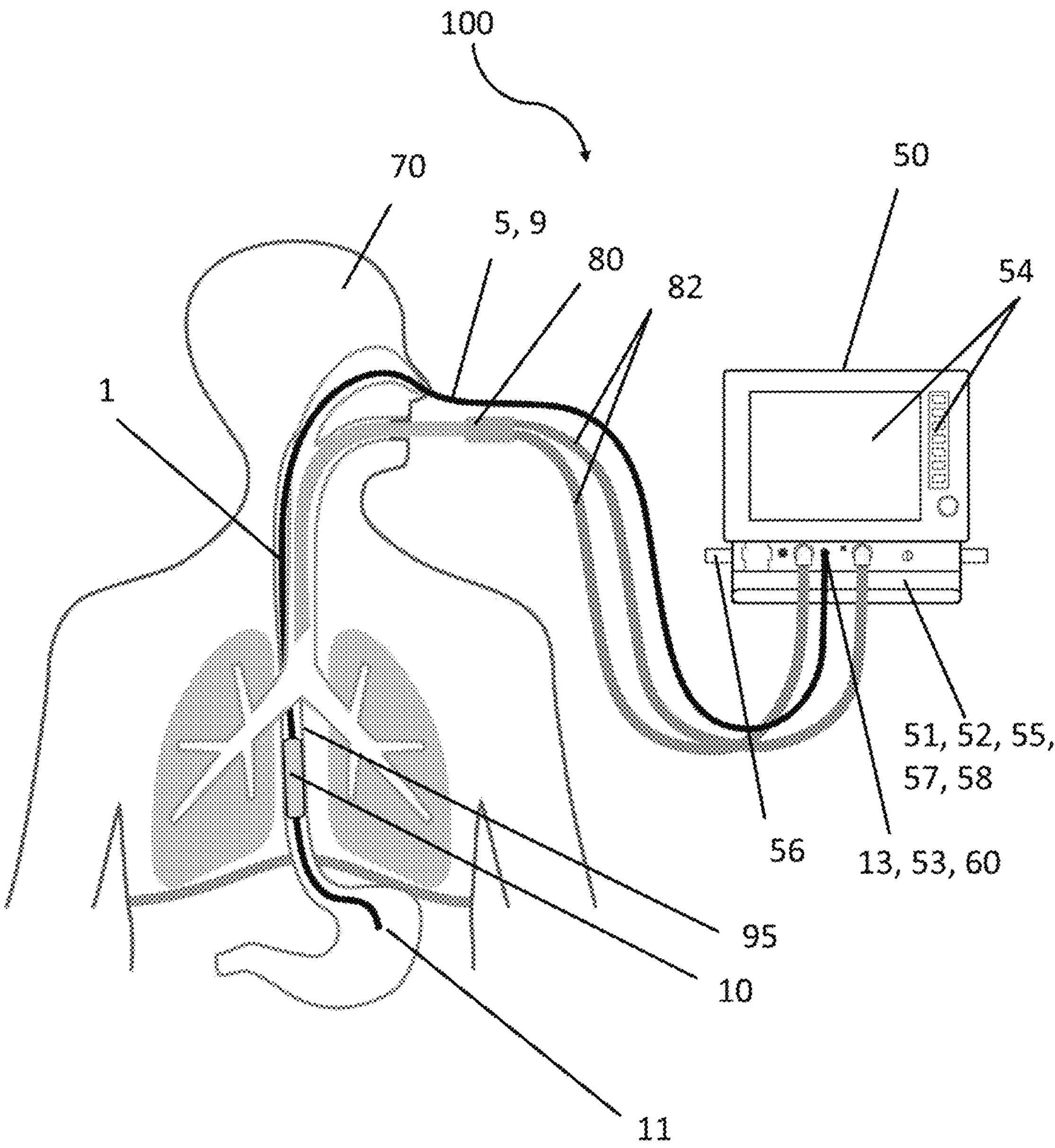
FIG. 1 shows the fundamental structure of a system according to the invention.

FIG. 1 shows the fundamental structure of a system 100 according to the invention.

The system 100 comprises a pressure ascertainment device 1, at least one pressure source 57, and at least one line 5. The pressure ascertainment device is designed as a medical catheter 1. The catheter 1 is preferably an esophageal catheter. The at least one line is designed as a pressure line 5.

The pressure source 57 can be configured and designed to be used as a pressure source and/or as a suction source. The pressure source 57 can apply pressure and/or dissipate pressure. Pressure source and suction source can also be formed as separate units in some embodiments. In some embodiments, the pressure source 57 can alternatively or additionally also be designed as a volume source. The pressure source 57 can thus also apply volume and/or remove or dissipate volume.

The pressure source 57 is preferably a ventilator 50 or is integrated in a ventilator 50. The pressure source 57 can also be an anesthesia machine or can be integrated in an anesthesia machine.

The catheter 1 comprises at least one esophagus balloon 10, which is designated hereinafter as balloon 10. Moreover, the catheter 1 comprises a hose 9 having a wall 8 and a lumen. The at least one pressure line 5 extends at least in sections in the lumen and/or in the wall 8 of the hose 9. The pressure line 5 is connected to the balloon 10. The pressure line 5 ends in the balloon 10 of the catheter 1.

The catheter 1 moreover comprises a pneumatic interface 13. The pneumatic interface 13 is located at one end of the catheter 1. The pneumatic interface 13 is located in a usage state outside the patient at the distal end of the catheter 1. The catheter 1 can be connected to the ventilator 50 via the pneumatic interface 13. The pneumatic interface 13 can comprise a switching valve, which can be designed, for example, as a three-way valve (not shown).

To be able to pneumatically connect the ventilator 50 to the catheter 1, the ventilator 50 can have a catheter fitting 53. The catheter 1 can be pneumatically connected to the ventilator 50 via the pneumatic interface 13 and the catheter fitting 53.

The pressure line 5 then runs from the ventilator 50 to the catheter 1. The pressure line 5 begins at the pressure source 57 of the ventilator 50 and ends at the balloon 10 of the catheter 1. The catheter 1 can thus be pneumatically connected to the ventilator 50. The balloon 10 of the catheter 1 is pneumatically connected via the pressure line 5 and the pneumatic interface 13 to the ventilator 50. The balloon 10 can be filled via the pressure line 5. The balloon 10 can moreover be emptied via the pressure line 5. The balloon 10 can be filled using a predetermined pressure and/or volume. The balloon 10 can be emptied using a predetermined pressure and/or volume. The pressure and/or the volume can be applied completely or step-by-step. The emptying can take place actively, wherein pressure and/or volume can be actively discharged from the balloon 10. The pressure and/or the volume can also be discharged passively.

A ventilator 50 is to be understood to mean all devices which assist a user or patient 70 in the natural respiration and/or take over the ventilation of a user or patient 70 and/or are used for respiratory therapy and/or act in another way on the respiration of a user or patient 70. These include, for example, but not exclusively, CPAP and BiLevel devices, narcosis or anesthesia machines, respiratory therapy devices, clinical, home, or emergency ventilators, high-flow treatment devices, and coughing machines.

The ventilator 50 can have an operating and information system 54. The required pressure and/or flow and/or the volume can be set and the present pressure and/or flow and/or the present volume can be displayed via the operating and information system 54. This user information can be graphically visualized or numerically represented, for example.

The ventilator 50 includes the at least one pressure source 57 (not shown) and a control unit 58. The pressure source 57 is designed as a pressure and/or suction source. The pressure source 57 can build up a pressure and/or dissipate or reduce it. The pressure source 57 can also be designed as a volume source. The pressure source 57 can apply a volume and/or remove or dissipate a volume.

The balloon 10 can be filled and emptied using the pressure source 57. The balloon 10 can be filled using a fluid via the pressure line 5. The balloon 10 can be filled using a predetermined pressure and/or volume. The fluid is in general a gas, for example, air and/or oxygen and/or a gas mixture and/or an oxygenated gas mixture. The balloon 10 is preferably manufactured from a flexible material impermeable to gas and water. For example, the balloon 10 is manufactured from latex.

In addition to the pressure source 57, the ventilator 50 can have a further pressure source, which is designed as a respiratory gas source 55. The respiratory gas source 55 can ensure the ventilation of the patient 70. The respiratory gas source 55 can provide a fluid for ventilation. For example, the respiratory gas source 55 can provide a gas and/or gas mixture. The respiratory gas source 55 can provide respiratory gas and/or oxygen and/or an oxygenated gas mixture and/or other suitable gases for ventilation. The respiratory gas source 55 is designed, for example, as an electric motor having fan wheel or as a pressurized gas fitting. For example, the respiratory gas source 55 can apply ventilation pressure 22 and/or flow and/or volume. The control unit 58 can specify the parameters of the ventilation in a controlled manner and/or at least partially in an assisted or adaptive manner in consideration of measurement signals.

The pressure source 57 for filling and/or emptying the balloon 10 and the respiratory gas source 55 for providing the ventilation pressure 22 are in general two different pressure sources, which are actuatable independently of one another. The pressure source 57 for filling and/or emptying the balloon 10 and the respiratory gas source 55 for providing the ventilation pressure 22 can also be one and the same device in some embodiments.

The ventilator 50 can additionally have at least one interface 56, via which a data transfer is possible.

The system 100 can contain further elements in addition to the pressure ascertainment device 1, the pressure source 50, and the pressure line 5.

In particular, the system 100 can be connected via a hose system 82 to a patient interface 80. A connection from the ventilator 50 to a patient 70 can be established via the patient interface 80, to ventilate said patient.

Any peripheral device which is designed for interaction with a living being is to be understood as a patient interface 80. In particular, the patient interface 80 is designed for treatment and/or diagnostic purposes in conjunction with the ventilator 50. The patient interface 80 can be designed as a breathing mask. This mask can be a full face mask, thus enclosing nose and mouth, or a nasal mask, thus a mask only enclosing the nose. Tracheal tubes or cannulas and so-called nasal glasses or nasal pillow masks can also be used as the patient interface 80. The system 100 according to the invention and method are also suitable in particular in conjunction with tracheal tubes or cannulas for invasive ventilation. The patient interface 80 and the ventilator 50 are preferably connected to one another in a gas-conducting manner via the at least one hose system 82. The hose system 82 is preferably made flexible and/or rotatable. The hose system 82 can be designed, for example, as an elastic tube and/or hose and/or hose system.

The system 100 can additionally comprise a fitting (not shown) for an invasive blood pressure measurement 86 and/or for temperature measurement. In addition, at least one external monitor 85 can be integrated in the system 100. Multiple external monitors 85 are also conceivable (not shown).

The system 100 is configured and designed to determine or ascertain an esophageal pressure 20 at least temporarily or in phases. The esophageal pressure 20 is used as a surrogate parameter for the pleural pressure 21. The changes of the esophageal pressure 20 during a breathing cycle reflect the changes of the pleural pressure 21.

Under machine ventilation, the inspiratory plateau pressure (Pplat) or the end-expiratory pressure (PEEP) are used as surrogate parameters for the calculation of the inspiratory or expiratory alveolar pressure, respectively, and the esophageal pressure 20 is used for the pleural pressure. In some embodiments, the system is additionally designed and configured to measure a gastric pressure 24, in order to be able to estimate the gastric pressure increases on the lung.

The control unit 58 is, for example, at least designed so that it can determine the esophageal pressure 20. The ventilator 50 has a pressure measurement input 51 and a sensor means 52 for determining the esophageal pressure 20. The pressure measurement input 51 can be designed, for example, pneumatically, electronically, and/or optically. The sensor means can be designed as a pressure sensor 52. The pressure sensor 52 is at least indirectly connected to the balloon 10. The esophageal pressure 20, which is detected via the gas-filled balloon 10 of the catheter 1, can be determined with the aid of the pressure sensor 52. The control unit 58 is, for example, configured and designed to identify a change of the esophageal pressure 20 and thereupon to actuate the ventilator 50 to specify a ventilation parameter.

If a threshold value for the esophageal pressure 20 is exceeded or undershot, the control unit 58, for example, generates a control signal for the ventilator 50, to specify an inspiratory or expiratory respiratory gas pressure. If a threshold value for the esophageal pressure 20 is exceeded or undershot, the control unit 58, for example, alternatively generates a control signal for the ventilator 50, to end the specification of an inspiratory or expiratory respiratory gas pressure.

FIG. 1 schematically shows the arrangement of the ventilator 50 in the system 100. The measurement of the esophageal pressure 20, also called Peso herein, is based on the use of the esophagus balloon 10. The esophageal pressure 20 is used as a surrogate parameter and reflects the changes of the pleural pressure 21. The pleural pressure 21, also called intrathoracic pressure, is the differential pressure between the pressure prevailing in the pleural cavity and the external pressure.

The transpulmonary pressure 23 can be determined or ascertained by computer progressively or in phases from the measured esophageal pressure 20 and a ventilation pressure 22 specified or measured by the ventilator 50.

The transpulmonary pressure 23 is that pressure which is required for the expansion of the lung and the chest wall. The transpulmonary pressure 23 corresponds to the pressure difference between the alveoli and the esophagus. For example, the transpulmonary pressure 23 can be determined upon end-inspiratory or end-expiratory occlusion.

The determination of the transpulmonary pressure 23 is thus enabled by the measurement of the esophageal pressure 20. The transpulmonary pressures 23 measured or determined progressively or in phases permit an evaluation of the mechanical pressure and volume stress under a ventilation, so that the ventilation can be adapted in a lung-protective manner. In addition, the monitoring of the esophageal pressure 20 helps in recognizing and treating the causes of ineffective patient exertions.

Figure 2:
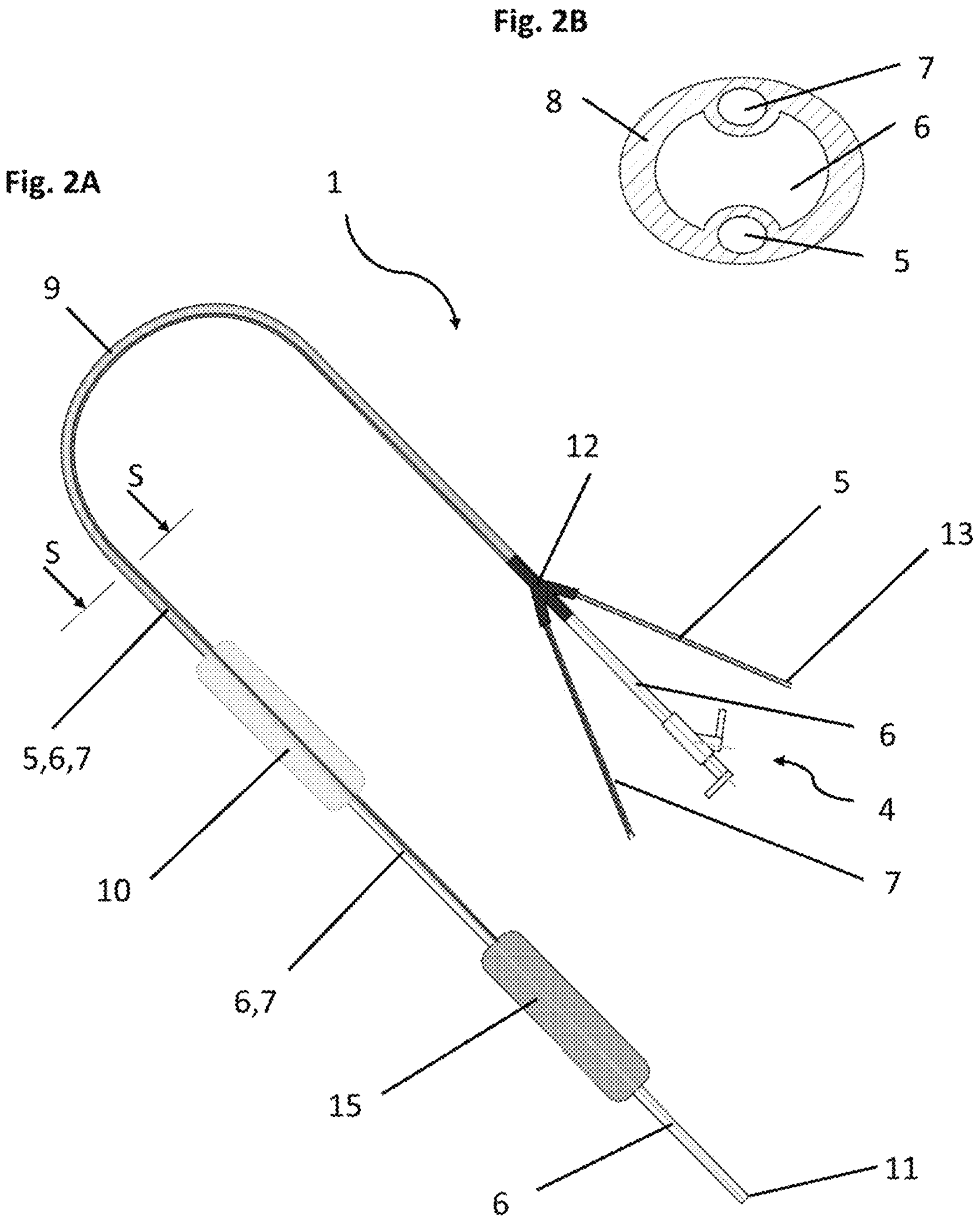
Figure 3:
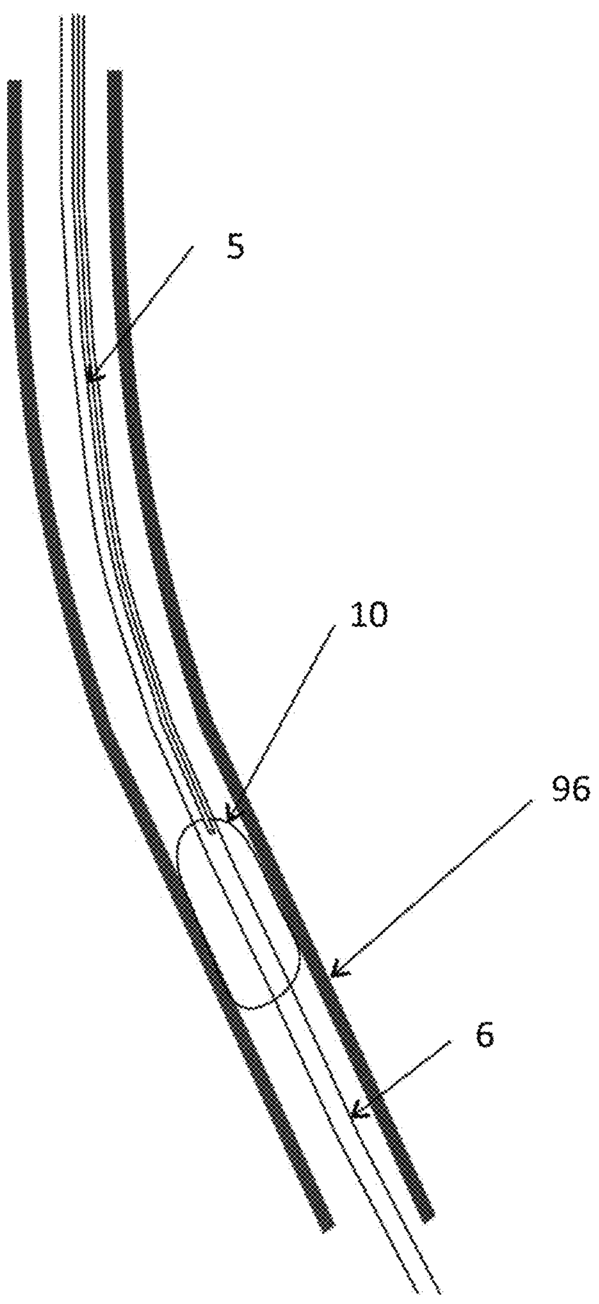
FIG. 3 shows a schematic depiction of an esophageal catheter placed in the esophagus.

FIG. 2 shows an esophageal catheter 1, wherein FIG. 2A shows a schematic side view of the catheter 1 and FIG. 2B shows a cross section according to line S-S through a section of the hose 9 of the catheter 1. FIG. 3 shows a schematic diagram of an esophageal catheter 1 placed in the esophagus 95.

The catheter 1 is designed as an esophageal catheter and comprises the at least one balloon 10 and the hose 9 and at least one line 5.

The line 5 extends at least in sections through the lumen of the hose 9 and/or the hose wall 8. The line 5 is designed as a pressure line 5 and is connected to the balloon 10. The pressure line 5 ends in the balloon 10 of the catheter 1. In addition to the pressure line 5, the catheter 1 can have further lines. The one or more lines generally do not communicate with one another and are arranged as separate lines in the lumen of the hose 9 and/or in its cavity 8 (see FIG. 2B).

In some embodiments, the catheter 1 can comprise a feeding line 6 and a fitting 4. The feeding line 6 extends, for example, from the fitting 4 over the entire length of the catheter 1 and ends in the esophagus 95 and/or in the stomach. The feeding line 6 preferably ends in the fundus of the stomach. The feeding line 6 and the fitting 4 are configured and designed to enable enteral feeding. The tube-suitable food can be introduced via the fitting 4 into the food line 6. The tube-suitable food reaches the body of the patient 70 via the feeding line 6. The feeding line 6 thus enables the direct supply of food into the stomach.

In some embodiments, the catheter 1 can comprise a gastric pressure line 7 and a gastric balloon 15. The gastric pressure line 7 can be connected to the gastric balloon 15. The gastric pressure line 7 ends in the gastric balloon 15 of the catheter 1. The gastric pressure line 7 and the gastric balloon 15 are configured and designed, for example, to measure the gastric pressure 24. For this purpose, the gastric pressure line 7 can be connected to the ventilator 50 (not shown). The gastric pressure 24 can be measured in the course of placing the catheter 1 to be able to estimate the gastric pressure increases on the lung. Optionally and/or additionally, the catheter 1 can have further lines. For example, a line for suctioning out stomach content is conceivable and/or a line for supplying medications (not shown).

In some advantageous embodiments of the catheter 1, a line can be provided for a guide wire 14 (not shown). The guide wire 14 can mechanically stiffen the catheter 1 from the inside. The insertion of the catheter 1 into the body of the patient 70 can be facilitated via the guide wire 14.

The catheter 1 shown by way of example in FIG. 2 has a pressure line 5, a feeding line 6, and a gastric pressure line 7 (see FIG. 2B).

The pressure line 5 ends in the balloon 10. The gastric pressure line 7 ends in the gastric balloon 15. The catheter 1 comprises a catheter end 11. The feeding line 6 ends at the catheter end 11. In a usage state, the catheter end 11 is arranged in or on the stomach or in the esophagus 95. The catheter end 11 is preferably arranged in the fundus of the stomach.

The catheter end 11 can be formed open. For example, tube-suitable food can be released via the open catheter end 11 from the feeding line 6 into the esophagus 95 and/or stomach. The tube-suitable food can preferably be released via the open catheter end 11 from the feeding line 6 into the fundus of the stomach.

It is also conceivable that stomach content can be received from the stomach and can be discharged from the stomach via the hose 9 and/or via a separate line in the hose 9 or in the hose wall 8.

Upon use of the catheter 1 on the patient, a part of the catheter 1 is located inside the body of a patient 70. The catheter 1 is inserted at least partially into the esophagus 95 of the patient 70. The catheter 1 is in a usage state when the catheter end 11 and at least a part of the hose 9 and the at least one balloon 10 are located in the esophagus 95 and/or in the stomach of the patient. In a usage state, the catheter end 11 is preferably located in the fundus of the stomach and at least a part of the hose 9 and the balloon 10 are located in the esophagus 95 of the patient.

The catheter 1 can comprise at least one distributor 12. The distributor 12 is located outside the body of the patient 70 in a usage state. The distributor 12 can represent an interface at which different lines 5,6,7 are guided together or away from one another.

The system 100 can have a valve 60 (FIG. 1). The valve 60 is preferably arranged outside the body of a patient 70 in a usage state of the catheter 1. The valve 60 can preferably be arranged in or on the ventilator 50. The valve 60 can also be arranged in or on the pressure line 5 in some embodiments. The valve 60 is configured and designed to conduct a defined volume of the pressure source 57 of the ventilator 50 into the balloon 10. The balloon 10 can be filled via the valve 60. The valve 60 is additionally configured and designed to conduct a defined volume out of the balloon 10 into the ventilator 50. The balloon 10 can be emptied via the valve 60.

The filling and emptying can preferably take place via a valve 60. In some embodiments, it is also conceivable that the filling and emptying take place via two or more valves 60. The filling and/or emptying take place via the pressure line 5. The aeration takes place via the pressure line 5 from the ventilator 50 to the balloon 10. The emptying takes place via the pressure line 5 from the balloon 10 to the ventilator 50.

The catheter 1 can comprise at least one of the following functions:

- measuring the esophageal pressure 20, which reflects the pleural pressure 21
- feeding the patient
- suctioning out stomach content
- detecting the pulsation of the heart
- measuring the gastric pressure 24

The system 100 is designed and configured to ascertain, set, and maintain a filling volume VB of esophagus balloons 10. The system 100 is in particular designed and configured to ascertain, set, and maintain an optimal filling volume VBopt of esophagus balloons 10. The system 100 is additionally designed and configured to ascertain a minimum filling volume VBa and/or a maximum filling volume VBe of esophagus balloons 10.

According to the invention, a method is provided for ascertaining and setting a filling volume VB of a balloon 10 of a catheter 1, which is placed in the esophagus 95 of a living being, wherein the balloon 10 is filled and/or emptied using a fluid. Different balloon volumes VB can be applied and balloon pressures PB can be ascertained for this purpose.

To ascertain the esophageal pressure 20, the filling volume VB of the balloon 10 is preferably selected in such a way that the balloon pressure PB corresponds to the esophageal pressure 20. The esophageal pressure 20 supplies items of information about pressure changes in the chest cavity between the lung and the chest wall and can be used as a surrogate parameter for the pleural pressure 21.

The balloon pressure PB corresponds to the esophageal pressure 20 when the filling volume VB is set sufficiently low that the perfusion of the inner wall of the esophagus 95 is not impaired and is set sufficiently high that the balloon wall presses against the esophageal wall 96 in such a way that reliable measurement results can be obtained.

Accordingly, there are a minimum filling volume VBa and a maximum filling volume VBe for the balloon 10 of an esophageal catheter 1. The balloon 10 is to be filled at least using the minimum filling volume VBa and at most using the maximum filling volume VBe, so that the balloon pressure PB corresponds to the esophageal pressure 20 and reliable measurement results can be obtained. The minimum filling volume VBa can be ascertained via the method. In addition, the maximum filling volume VBe of the balloon 10 can be ascertained via the method.

The method according to the invention is used in particular to ascertain an optimum filling volume VBopt of the balloon 10. The measurement of the esophageal pressure 20 is particularly valid if the balloon 10 is filled using the optimum filling volume VBopt. The optimum filling volume VBopt is in a range between the minimum filling volume VBa and the maximum filling volume VBe.

The method according to the invention is described hereinafter. The method is preferably carried out using a catheter 1, which is placed in a human. The method is carried out, for example, under controlled bilevel ventilation. Alternatively or additionally, the method can also be carried out under spontaneous respiration.

The catheter 1 is placed in the patient. The balloon 10 of the catheter 1 is placed in the esophagus 95. The balloon 10 of the catheter 1 can be placed anywhere in the esophagus 95. The balloon 10 is preferably placed in the bottom to middle third of the esophagus (see FIG. 3). The balloon 10 is particularly preferably placed in the middle third of the esophagus.

Initially, the balloon 10 is filled using a standard volume VB0 specified by the manufacturer. The standard volume VB0 of commercially available esophagus balloons 10 is generally—depending on the size and length of the balloon 10—between approximately 0.5 mL and approximately 5 mL. For example, the balloon 10 is initially filled using a standard volume VB0 of 3 mL of fluid.

An initial pressure adjustment subsequently takes place. For this purpose, different balloon volumes VB are applied and the corresponding balloon pressures PB are measured.

The balloon 10 is initially emptied again. The emptying is preferably carried out completely. Complete emptying is provided when no fluid is still located in the balloon 10. In the case of complete emptying, the volume is ideally 0 mL.

At least one breath is waited out before the balloon 10 is filled again. Preferably, more than one breath is waited out. For example, 3 or 4 breaths are waited out. More than 4 breaths can also be waited out.

After at least one breath has been waited out, the balloon 10 is filled again. The filling preferably takes place step-by-step. Step-by-step filling means that the balloon 10 is repeatedly filled using a defined volume. The step-by-step filling takes place additively. No emptying takes place between the steps.

The step-by-step filling and/or emptying takes place using predetermined volume steps Vi. The volume steps Vi can always have the same value, for example. In some embodiments, the volume steps Vi can also have different values.

The volume steps Vi for the individual filling steps are in a range from approximately 0.1 mL to approximately 2 mL. The balloon 10 is preferably filled in volume steps Vi of approximately 0.2 mL to approximately 0.8 mL. For example, the balloon 10 is filled in volume steps Vi of approximately 0.5 mL.

After each volume step Vi, at least one breath is waited out before the balloon 10 is filled using a further volume step Vi. Preferably, more than one breath is waited out. For example, 3 or 4 breaths are waited out. More than 4 breaths can also be waited out, for example, up to 10 breaths or more.

The filling takes place up to a final volume VB1. At the final volume VB1, the balloon 10 is slightly overfilled or overinflated. For example, the balloon 10 is slightly overfilled at an esophageal pressure 20 of approximately 30 mbar. For example, the balloon 10 is filled step-by-step up to a final volume VB1 of approximately 10 mL.

After reaching a balloon pressure PB of, for example, 30 mbar and/or after reaching a final volume VB1 of, for example, approximately 10 mL, the balloon is emptied again.

The emptying takes place step-by-step. Step-by-step emptying means that a defined volume is repeatedly removed from the balloon 10. No filling takes place between the individual steps of the step-by-step emptying. The emptying takes place completely. The emptying takes place until the volume of the balloon 10 is ideally again at 0 mL.

The step-by-step emptying takes place using predetermined volume steps Vi. The volume steps Vi for the step-by-step emptying are in a range from approximately 0.1 mL to approximately 2 mL. The balloon 10 is preferably emptied in volume steps Vi of approximately 0.2 mL to approximately 0.8 mL. For example, the balloon 10 is emptied in volume steps Vi of approximately 0.5 mL. The volume Vi of the emptying steps is preferably equal to the volume Vi of the filling steps. The volume Vi of the emptying steps can in some embodiments of the method be greater or less than the volume Vi of the filling steps.

After each emptying step, at least one breath is waited out before the balloon 10 is emptied using a further volume step Vi. Preferably, more than one breath is waited out. For example, 3 or 4 breaths are waited out. More than 4 breaths can also be waited out.

The number of the breaths to be waited out after each emptying step is preferably equal to the number of the breaths to be waited out after each filling step. However, more or fewer breaths can also be waited out after each emptying step than after each filling step.

After the individual filling steps and/or emptying steps, in each case at least one breath is waited out to reduce oscillation artifacts of the balloon 10.

The balloon pressure PB can be continuously ascertained during the filling and/or emptying of the balloon 10. The balloon pressure PB can be ascertained for each individual volume step Vi of the filling and/or emptying. For example, the balloon pressure PB is ascertained at least upon one breath per each volume step Vi of the filling and/or emptying. The balloon pressure PB is preferably ascertained for all breaths.

The balloon pressure PB is preferably ascertained at the end of the inspiration (Pmax) and at the end of the expiration (Pmin).

The pressure values Pmin and Pmax can be analyzed to ascertain the minimum filling volume VBa and the maximum filling volume VBe. The values Pmin and Pmax can additionally be analyzed to ascertain the optimum filling volume VBopt. The balloon pressure PB can be analyzed in dependence on the filling volume VB.

The ascertained balloon pressures PB per volume step Vi of the filling and/or emptying can be individually evaluated or averaged. For example, on the one hand, the mean value of Pmax per volume step Vi is ascertained and, on the other hand, the mean value of Pmin per volume step Vi. For the averaging, all or only a few selected balloon pressures PB can be used. Alternatively or additionally to the mean value, medians, percentiles, derivatives, frequency distributions, or the like can also be ascertained from the measured values of the balloon pressures PB and used as the basis of the further calculation.

The measured values Pmax and Pmin, which are obtained in above-mentioned procedures, can be analyzed. Ascertaining a pressure difference ΔPB between Pmax and Pmin is advantageous. This pressure difference ΔPB is also referred to as Delta-Peso.

The pressure difference ΔPB is preferably ascertained for each volume step Vi of the filling and/or emptying. In particular, the pressure differences ΔPB between Pmax and Pmin of respectively identical filling and/or emptying steps can be ascertained. The change of the pressure differences ΔPB between Pmax and Pmin are an indicator of when the balloon pressure PB corresponds to the esophageal pressure 20.

The ascertained measured values can be analyzed and, for example, graphically represented. The balloon pressure PB at the end of the expiration Pmin and/or the balloon pressure PB at the end of the inspiration Pmax can be analyzed, for example, as a function of the filling volume VB. The measured values can be represented, for example, in an axis diagram (see FIG. 4).

Figure 4:
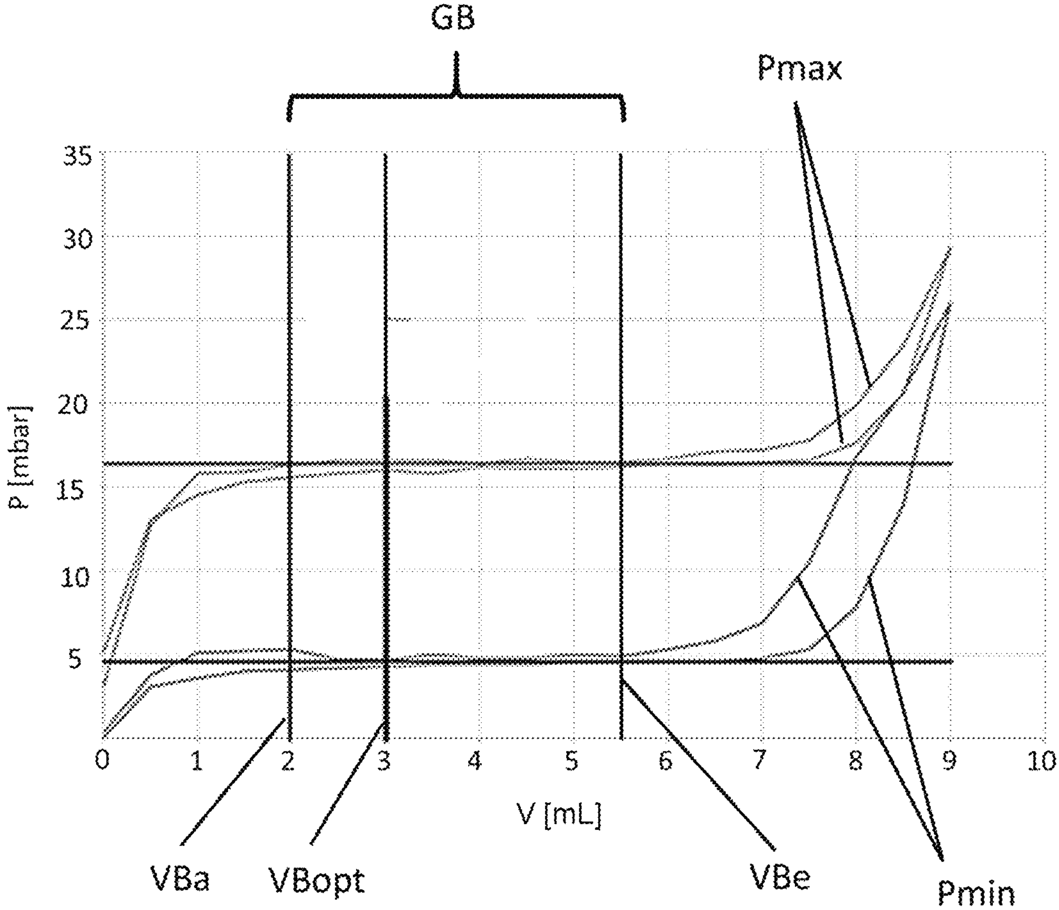
FIG. 4 shows a graphic representation of an exemplary pressure-volume behavior of an esophageal catheter in vitro.

FIG. 4 shows a graphic representation of an exemplary pressure (P)—volume (V) behavior of an esophageal catheter 1 in vitro. In vitro studies of esophageal catheters 1 display a typical hysteresis with respect to their pressure—volume behavior.

On the X axis, the volume V, namely the filling volume VB of the balloon 10, is plotted in mL. On the Y axis, the pressure P, namely the balloon pressure PB, is plotted in mbar.

Pressure differences ΔPB between Pmax and Pmin are apparent from FIG. 4. These pressure differences ΔPB are also referred to herein as Delta-Peso. The Delta-Peso describes the pressure difference between Pmax and Pmin as a function of the filling volume VB.

It is apparent from FIG. 4 that the curves of Pmin and Pmax extend nearly in parallel in the range of 2 mL to 5.5 mL filling volume VB. A plateau forms, thus a region in which Pmin and Pmax do not significantly change in relation to one another.

The change of the pressure differences ΔPB between Pmax and Pmin is an indicator of when the balloon pressure PB corresponds to the esophageal pressure 20. The pressure difference ΔPB is the difference between Pmax and Pmin.

The pressure difference ΔPB can be calculated as follows, for example:

$$\Delta PB = P_{max} - P_{min}$$

The pressure difference ΔPB from one volume step Vi of the step-by-step filling and/or emptying to the next volume step Vi+1 can be ascertained, for example, as a percentage value or index value to ascertain a relative pressure difference rΔPB.

The volume step Vi is in this case the volume of the ith volume step (filling or emptying step). The volume step Vi+1 is the volume of the following volume step (filling or emptying step). The pressure differences ΔPB of successive volume steps (Vi, Vi+1) are related to one another, so that a percentage deviation can be ascertained.

The relative pressure difference rΔPB can be ascertained, for example, using the following formula:

$$r\Delta PB = \left|\frac{\Delta PB(Vi+1) - \Delta PB(Vi)}{\Delta PB(Vi+1)}\right| * 100\%$$

A border range GB can be identified on the basis of the relative pressure difference rΔPB. Within the border range GB, the progress curves of Pmin and Pmax run nearly constant. Within the border range GB, Pmin and Pmax of the successive volume steps Vi do not significantly deviate from one another. Moreover, the curves of Pmin and Pmax run approximately in parallel to one another within the border range GB. Within the border range GB, the pressure difference ΔPB is therefore approximately constant (see FIG. 4).

The border range GB is significantly less than 100%, preferably less than approximately 50%, particularly preferably less than approximately 25%. In a specific exemplary embodiment, the border range GB is in a range from 0 to approximately 10% inclusive (not shown).

If the relative pressure difference rΔPB is greater than the border range GB, the balloon pressure PB is outside the esophageal pressure 20 and is not suitable for measuring the esophageal pressure 20. If the relative pressure difference rΔPB is within the border range GB, the balloon pressure PB corresponds to the esophageal pressure 20 and is suitable for measuring the esophageal pressure 20.

The minimum filling volume VBa and the maximum filling volume VBe can thus be derived from a step-by-step filling and emptying of the balloon 10.

The minimum filling volume VBa is present when after a volume step Vi, the relative pressure difference rΔPB is within the border range GB for the first time. The minimum filling volume VBa is thus present when it does not fall below the minimum value of the border range GB.

The minimum filling volume VBa is thus at the beginning, from which Pmax and Pmin run nearly in parallel. The relative pressure difference rΔPB at the minimum filling volume VBa is defined by the upper end of the border range GB. In one specific embodiment, the relative pressure difference rΔPB at the minimum filling volume VBa can be at 10%.

The maximum filling volume VBe is present at the volume step Vi at which the relative pressure difference rΔPB is within the border range GB for the last time. The maximum filling volume VBe is thus present when it does not exceed the minimum value of the border range GB.

The maximum filling volume VBe is thus at the end, from which Pmax and Pmin run nearly in parallel and run constant for the last time. The relative pressure difference rΔPB at the maximum filling volume VBa is also defined by the upper end of the border range GB. In one specific embodiment, the relative pressure difference rΔPB at the maximum filling volume VBe can be at 10%.

The relative pressure difference rΔPB at filling volumes which are greater than the maximum filling volume VBe is outside the border range GB.

Filling volumes which are less than the minimum filling volume VBa and/or greater than the maximum filling volume VBe are not suitable for a measurement of the esophageal pressure 20.

Filling volumes which are greater than the minimum filling volume VBa and/or less than the maximum filling volume VBe are suitable for a measurement of the esophageal pressure 20.

The optimum filling volume VBopt is in the range between the minimum filling volume VBa and the maximum filling volume VBe. In some embodiments, the optimum filling volume VBopt can also be equal to the minimum filling volume VBa or equal to the maximum filling volume VBe.

In one preferred embodiment, the optimum filling volume VBopt is greater than the minimum filling volume VBa and less than the maximum filling volume VBe.

When the balloon 10 is filled using the optimum filling volume VBopt, the balloon 10 has an optimum adjustment to the esophagus 95. The esophageal wall 96 is not negatively influenced by the balloon 10 filled using the optimum filling volume VBopt. Moreover, the balloon 10 supplies reliable, valid, reproducible measured values when it is filled using the optimum filling volume VBopt. The pressure changes in the balloon 10 reflect the esophageal pressure 20 and thus the pleural pressure 21 optimally. The pleural pressure 21 in turn reflects the pressure in the lung.

In some embodiments, the optimum filling volume VBopt is more than approximately 10% above the minimum filling volume VBa and less than approximately 80% below the maximum filling volume VBe. Preferably, the optimum filling volume VBopt is more than approximately 20% above the minimum filling volume VBa and less than approximately 50% below the maximum filling volume VBe. In one specific exemplary embodiment, the optimum filling volume VBopt is approximately 30% above the minimum filling volume VBa and approximately 70% below the maximum filling volume VBe.

The optimum filling volume VBopt can be calculated, for example, using the following formula:

$$VBopt = VBa + \frac{(VBe - VBa)}{3}$$

It is apparent from FIG. 4 that the minimum filling volume VBa in this specific exemplary embodiment is, for example, approximately 2 mL and the maximum filling volume VBe is, for example, approximately 5.5 mL. Between the minimum filling volume VBa and the maximum filling volume VBe, Pmin and Pmax are in a nearly constant range.

At a minimum filling volume VBa of, for example, 2 mL and a maximum filling volume VBe of, for example, 5.5 mL, the optimum filling volume VBopt is thus, for example, approximately 3.17 mL.

If optimum filling volume VBopt and the standard volume VB0 set at the beginning are not equal and the initial pressure adjustment is no longer carried out, the balloon pressure BP can thus be corrected. The balloon 10 can be set using the ascertained optimum filling volume VBopt.

Alternatively and additionally, a pressure correction of the optimum filling volume VBopt can be performed. The pressure correction corrects the optimum filling volume VBopt with incorporation of the esophageal compliance Ces.

The esophageal compliance Ces is the elastic volume extensibility of the esophagus 95. Because the esophageal wall 96 has an extensibility, the balloon pressure PB becomes greater upon an enlargement of the balloon 10 and less upon a reduction in size of the balloon 10. In vivo, instead of a plateau, a linearly rising pressure profile can thus result, which is caused by the esophageal compliance Ces (not shown). The esophageal compliance Ces of the esophagus 95 is not uniform in vivo and can vary depending on the section of the esophagus 95. For the method according to the invention, the esophageal compliance Ces can be presumed to be constant by way of example.

In some embodiments, the esophageal compliance Ces is newly ascertained at regular intervals. It can be provided that the esophageal compliance Ces is additionally or alternatively newly ascertained at least when it is established that the filling volume VB of the balloon 10 is outside the border range GB or the border range GB changes so that the filling volume VB is outside the border range GB at least once.

A relationship exists between the change of the filling volume ΔVB and the change of the balloon pressure ΔPB due to the esophageal compliance Ces. The wall displacement of the esophagus 95 by the balloon 10 can be depicted by the following formula: ΔVB=Ces*ΔPB For the volume range which comes into consideration for a measurement of the esophageal pressure 20, the esophageal compliance Ces is presumed to be constant.

To ascertain the esophageal compliance Ces, the minimum filling volume VBa and the maximum filling volume VBe are used as well as the pressures at the end of the expiration Pmin. PBEa is the balloon pressure at the end of the expiration at the minimum filling volume VBa. PBEe is the balloon pressure at the end of the expiration at the maximum filling volume VBe.

The esophageal compliance Ces can be calculated, for example, on the basis of the following formula:

$$Ces = \frac{VBe - VBa}{PBEe - PBEa}$$

A more accurate calculation is achieved if a linear regression is carried out over the volume range between the minimum filling volume VBa and the maximum filling volume VBe. According to the formula ΔVB=Ces*ΔPB, the pressure correction can be applied as follows.

For the case that the optimum filling volume VBopt is greater than the standard volume VB0, the following can apply:

$$\Delta PB = Ces(VBopt - VB0)$$

For the case that the optimum filling volume VBopt is less than the standard volume VB0, the following can apply:

$$\Delta PB = Ces(VB0 - VBopt)$$

The optimum filling volume VBopt and a corrected optimum filling volume VBoptcorr can be ascertained via the method according to the invention. The balloon 10 can thus be filled using the optimum filling volume VBopt. Preferably, the balloon 10 can be filled using the corrected optimum filling volume VBoptcorr which takes into consideration the esophageal compliance Ces.

Alternatively or additionally, the ratio between applied filling volume VB and the balloon pressure PB can be monitored to detect and compensate for a possible leak.

Although the present invention was described in detail on the basis of the exemplary embodiments, it is self-evident to a person skilled in the art that the invention is not restricted to these exemplary embodiments. Rather, modifications are possible in such a way that individual features are omitted or different combinations of the described individual features can be implemented if the scope of protection of the appended claims is not left. The present disclosure also includes all combinations of the presented individual features.

| List of reference signs | |
|---|---|
| 1 | catheter |
| 4 | fitting |
| 5 | pressure line |
| 6 | feeding line |
| 7 | gastric pressure line |
| 8 | hose wall |
| 9 | hose |
| 10 | balloon |
| 11 | catheter end |
| 12 | distributor |

-continued

| List of reference signs | |
|---|---|
| 13 | pneumatic interface |
| 14 | guide wire |
| 15 | gastric balloon |
| 20 | esophageal pressure (Peso) |
| 21 | pleural pressure (intrathoracic pressure) |
| 22 | ventilation pressure (PAW) |
| 23 | transpulmonary pressure (TPP) |
| 24 | gastric pressure |
| 50 | ventilator |
| 51 | pressure measurement input |
| 52 | pressure sensor |
| 53 | catheter fitting |
| 54 | operating and information system |
| 55 | respiratory gas source |
| 56 | interface |
| 57 | pressure source |
| 58 | control unit |
| 60 | valve |
| 70 | patient |
| 80 | patient interface |
| 82 | hose system |
| 85 | external monitor |
| 86 | fitting for invasive blood pressure measurement |
| 95 | esophagus |
| 96 | esophageal wall |
| 100 | system |
| Ces | esophageal compliance |
| GB | border range |
| P | pressure |
| PB | balloon pressure |
| Pmax | balloon pressure at the end of the inspiration |
| Pmin | balloon pressure at the end of the expiration |
| ΔPB | pressure difference between Pmax and Pmin/Delta-Peso |
| rΔPB | relative pressure difference |
| S | plane of section |
| V | volume |
| VB | filling volume |
| VB0 | standard volume |
| VB1 | end volume |
| Vi | volume step (filling step/emptying step) |
| VBa | minimum filling volume |
| VBe | maximum filling volume |
| VBopt | optimum filling volume |
| VBoptcorr | corrected optimum filling volume |
| ΔVB | volume difference |

What is claimed is:

1. A method for ascertaining and setting a filling volume VB of a balloon of a catheter, which is placed in the esophagus of a living being, wherein the balloon is filled and/or emptied using a fluid, the method comprising step-by-step filling and/or emptying of the balloon using at least two volume steps Vi;

determining a pressure difference ΔPB between a pressure at an end of an expiration Pmin and a pressure at an end of an inspiration Pmax for at least two volume steps Vi;

determining a relative pressure difference rΔPB between Pmin and Pmax;

defining a border range GB on the basis of the relative pressure difference rΔPB;

ascertaining an optimum filling volume VBopt in consideration of the border range GB.

2. The method of claim 1, wherein the balloon is filled and/or emptied via at least one pressure source which provides fluid in the form of a gas and fills and/or empties the balloon using gas.

3. The method of claim 1, wherein the balloon is initially filled using a standard volume VB0 and is subsequently completely emptied.

4. The method of claim 1, wherein the balloon, after having been emptied, is filled step-by-step with gas using at least two volume steps Vi until the balloon is slightly overinflated.

5. The method of claim 1, wherein the balloon is filled step-by-step with gas until the balloon has a balloon pressure PB of from 10 mbar to 40 mbar.

6. The method of claim 1, wherein the balloon is emptied step-by-step using at least two volume steps Vi until the balloon no longer contains gas.

7. The method of claim 1, wherein the balloon is filled or emptied in each volume step Vi using 0.1 mL to 2 mL gas.

8. The method of claim 1, wherein after at least one volume step Vi, at least one breath is waited out in each case before the balloon is filled and/or emptied using a further volume step Vi.

9. The method of claim 1, wherein a balloon pressure PB is ascertained at the end of the expiration Pmin and/or at the end of the inspiration Pmax of each breath of each volume step Vi.

10. The method of claim 1, wherein the pressure difference APB between the pressure at the end of the expiration Pmin and the pressure at the end of the inspiration Pmax is ascertained for at least one volume step Vi.

11. The method of claim 1, wherein the relative pressure difference rAPB from one volume step Vi to a next volume step Vi+1 is ascertained as a percentage value or index value.

12. The method of claim 1, wherein the border range GB is a percentage value or index value, the border range GB being less than 100% and the pressures of Pmin and Pmax running nearly constant and in parallel to one another within the border range GB.

13. The method of claim 1, wherein the border range GB is in a range from greater than 0% to 10% inclusive.

14. The method of claim 1, wherein a minimum filling volume VBa and/or a maximum filling volume VBe are ascertained on the basis of the border range GB.

15. The method of claim 1, wherein a filling volume VB at which the relative pressure difference rΔPB is within the border range GB for a first time is defined as a minimum filling volume VBa and wherein a filling volume VB at which the relative pressure difference rΔPB is within the border range GB for a last time is defined as a maximum filling volume VBe.

16. The method of claim 15, wherein the optimum filling volume VBopt is defined in a range between the minimum filling volume VBa and the maximum filling volume VBe.

17. The method of claim 15, wherein the optimum filling volume VBopt is more than 10% above the minimum filling volume VBa and less than 80% below the maximum filling volume VBe.

18. The method of claim 1, wherein an esophageal compliance Ces is ascertained on the basis of a balloon pressure at an end of an expiration Pmin with a minimum filling volume VBa and on the basis of a balloon pressure at an end of an expiration Pmin with a maximum filling volume VBe.

19. The method of claim 18, wherein a corrected optimum filling volume VBoptcorr is ascertained with incorporation of the ascertained esophageal compliance Ces and the optimum filling volume VBopt.

* * * * *